US008323936B2

(12) United States Patent
Gupta et al.

(10) Patent No.: US 8,323,936 B2
(45) Date of Patent: Dec. 4, 2012

(54) PROCESS FOR THE ENANTIOSELECTIVE ENZYMATIC REDUCTION OF SECODIONE DERIVATIVES

(75) Inventors: Antje Gupta, Wiesbaden (DE); Anke Tschentscher, Eltville-Hattenheim (DE); Maria Bobkova, Wiesbaden (DE)

(73) Assignee: IEP GmbH, Wiesbaden (DE)

( * ) Notice: Subject to any disclaimer, the term of this patent is extended or adjusted under 35 U.S.C. 154(b) by 0 days.

(21) Appl. No.: 13/227,390

(22) Filed: Sep. 7, 2011

(65) Prior Publication Data

US 2012/0040424 A1 Feb. 16, 2012

Related U.S. Application Data

(63) Continuation of application No. 12/518,025, filed as application No. PCT/EP2007/010640 on Dec. 7, 2007.

(51) Int. Cl.
*C12P 7/38* (2006.01)
*C12N 9/02* (2006.01)

(52) U.S. Cl. .......................................... 435/149; 435/189

(58) Field of Classification Search ........................ None
See application file for complete search history.

(56) References Cited

U.S. PATENT DOCUMENTS

| 1,252,524 | A |  | 1/1918 | White |
| 3,616,225 | A |  | 10/1971 | Isono et al. |
| 3,616,226 | A |  | 10/1971 | Isono et al. |
| 3,697,379 | A |  | 10/1972 | Buzby, Jr. et al. |
| 5,200,335 | A |  | 4/1993 | Hummel et al. |
| 5,523,223 | A |  | 6/1996 | Kula et al. |
| 5,763,236 | A |  | 6/1998 | Kojima et al. |
| 6,645,746 | B1 | * | 11/2003 | Kizaki et al. .................. 435/189 |

FOREIGN PATENT DOCUMENTS

| DE | 19610894 | 9/1997 |
| DE | 10119274 | 10/2002 |
| DE | 10327454 | 1/2005 |
| WO | 2006/087235 A1 | 8/2006 |

OTHER PUBLICATIONS

K. Abokitse, et al "Cloning, sequence analysis, and heterologous expression of the gene encoding a (S_-specific alcohol dehydrogenase from *Rhodococcus erythropolis* DSM 43297" Appl Microbiol Biotechnol (2003) 62:380-386.
Curt Bradshaw, et al "*Lactobacillus kefir* Alcohol Dehydrogenase: A Useful Catalyst for Synthesis" J. Org. Chem. 1992, vol. 57, No. 5, pp. 1532-1536.
P. Hildebrandt, et al "Cloning, functional epxressino and biochemical characterization of a stereoselective alcohol dehydrogenase from *Pseudomonas fluorescens* DSM50106" Appl Microbiol Biotechnol (2002) vol. 59, pp. 483-487.
H. Kosmol, et al "Mikrobiologische sterospezifische Reduktion vol. 3-Methoxy-8.14-seco-1.3.5(10).9-ostratetraen-14.17-dion)" Liebigs Ann. Chem. 701 (1967) pp. 199-205.
I. Mehdi, et al "Microbial transformation of 12-ethyl-3-methoxy-8, 14-seco-gona-1,3,5(10),9(11)-tetraerfe-14, 17-dione to its 17-βhyrdoxy derivative by *Pichia farinosa* in pilot plant fermentors" Indian Journal of Experimental Biology, vol. 27, Aug. 1989, pp. 742-743.
Karsten Niefind, et al "Cyrstallization and preliminary characterization of crystals of R-alcohol dehydrogenase from *Lactobacillus brevis*" Acta Crystallography, (2000), D56, pp. 1696-1698.
Jorg Peters, et al "A novel NADH-dependent carbonyl reductase with an extremely broad substrate range from *Candida parapsilosis*: Purification and characterization" Enzyme Mircrob. Technol., 1993, vol. 15, November, pp. 950-958.
Wolfgang Stampfer, et al "Biocatalytic Asymmetric Hydrogen Transfer Employing *Rhodococcus ruber* DSM 44541" J. Org. Chem., 2003, vol. 68, pp. 402-406.
A. Szentirmai, et al "Properties of Hydroxysteroid Oxidoeductase Isolated From Yeast" Acta Microbiol. Acad. Schi. hung. vol. 22, pp. 463-471 (1975).
Sheng-Xue Xie, et al "NAD+-Dependent (S)-Specific Secondary Alcohol Dehydrogenase Involved in Stereoinversion of 3-Pentyn-2-ol Catalyzed by *Nocardia fusca* AKU 2123" Biosci. Biotechnol. Biochem., vol. 60, No. 10 (1999), pp. 1721-1729.

* cited by examiner

*Primary Examiner* — Tekchand Saidha
*Assistant Examiner* — MD. Younus Meah
(74) *Attorney, Agent, or Firm* — Workman Nydegger

(57) ABSTRACT

The invention relates to a process for the enantioselective enzymatic reduction of secodione derivatives. The secodione derivative is reduced with an oxidoreductase/dehydrogenase in the presence of NADH or NADPH as a cofactor. The secodione derivative is used in the reaction batch at a concentration of $\geq 10$ g/l and the oxidized cofactor NAD or NADP formed by the oxidoreductase/dehydrogenase is regenerated continuously.

12 Claims, No Drawings

SEQUENCE LISTING

<160> NUMBER OF SEQ ID NOS: 42

<210> SEQ ID NO 1
<211> LENGTH: 252
<212> TYPE: PRT
<213> ORGANISM: Chloroflexus auratiacus DSM 635

<400> SEQUENCE: 1

```
Met Glu Pro Pro Phe Ile Gly Lys Val Ala Leu Val Thr Gly Ala Ala
1               5                   10                  15

Ala Gly Ile Gly Arg Ala Ser Ala Leu Ala Phe Ala Arg Glu Gly Ala
            20                  25                  30

Lys Val Val Val Ala Asp Val Asn Val Glu Gly Gly Glu Glu Thr Ile
        35                  40                  45

Ala Leu Cys Arg Ala Leu Asn Thr Asp Ala Met Phe Val Arg Cys Asp
    50                  55                  60

Val Ser Gln Arg Asp Glu Val Glu Arg Leu Ile Ala Leu Ala Val Asp
65                  70                  75                  80

Thr Phe Gly Arg Ile Asp Phe Ala His Asn Asn Ala Gly Ile Glu Gly
                85                  90                  95

Val Gln Ala Met Leu Ala Asp Tyr Pro Glu Glu Val Trp Asp Arg Val
            100                 105                 110

Ile Glu Ile Asn Leu Lys Gly Val Trp Leu Cys Met Lys Tyr Glu Ile
        115                 120                 125

Arg His Met Leu Lys Gln Gly Gly Ala Ile Val Asn Thr Ser Ser
    130                 135                 140

Val Ala Gly Leu Ala Gly Ser Arg Gly Val Ser Ala Tyr Val Ala Ser
145                 150                 155                 160

Lys His Gly Ile Val Gly Ile Thr Lys Ala Ala Ala Leu Glu Tyr Ala
                165                 170                 175

Arg Asn Gly Ile Arg Val Asn Ala Ile Cys Pro Gly Thr Ile His Thr
            180                 185                 190

Ala Met Ile Asp Arg Phe Thr Gln Gly Asp Pro Gln Leu Leu Ala Gln
        195                 200                 205

Phe Ala Glu Gly Glu Pro Ile Gly Arg Leu Gly Ser Pro Glu Glu Val
    210                 215                 220

Ala Asn Ala Val Ile Trp Leu Cys Ser Asp Lys Ala Ser Phe Val Thr
225                 230                 235                 240

Gly Ala Thr Leu Ala Val Asp Gly Gly Arg Leu Ala
                245                 250
```

<210> SEQ ID NO 2
<211> LENGTH: 249
<212> TYPE: PRT
<213> ORGANISM: Rubrobacter xylanophilus DSM 9941

<400> SEQUENCE: 2

| Met | Leu | Glu | Gly | Lys | Val | Ala | Val | Ile | Thr | Gly | Ala | Gly | Ser | Gly | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gly | Arg | Ala | Thr | Ala | Leu | Lys | Phe | Ala | Arg | Glu | Gly | Ala | Arg | Val | Val |
|     |     |     | 20  |     |     |     |     | 25  |     |     |     |     | 30  |     |     |

| Ala | Ala | Glu | Leu | Asp | Glu | Arg | Gly | Gly | Glu | Gly | Val | Val | Arg | Glu | Val |
|     |     | 35  |     |     |     |     | 40  |     |     |     |     | 45  |     |     |     |

| Arg | Ser | Leu | Gly | Gly | Glu | Ala | Val | Phe | Val | Arg | Thr | Asp | Val | Ser | Glu |
|     | 50  |     |     |     |     | 55  |     |     |     |     | 60  |     |     |     |     |

| Phe | Ala | Gln | Val | Glu | Asp | Ala | Val | Glu | Arg | Ala | Val | Gly | Glu | Tyr | Gly |
| 65  |     |     |     |     | 70  |     |     |     |     | 75  |     |     |     |     | 80  |

| Thr | Leu | Asp | Val | Met | Phe | Asn | Asn | Ala | Gly | Ile | Gly | His | Tyr | Ala | Pro |
|     |     |     |     | 85  |     |     |     |     | 90  |     |     |     |     | 95  |     |

| Leu | Leu | Glu | His | Glu | Pro | Glu | His | Tyr | Asp | Arg | Val | Val | Arg | Val | Asn |
|     |     |     | 100 |     |     |     |     | 105 |     |     |     |     | 110 |     |     |

| Gln | Tyr | Gly | Val | Tyr | Tyr | Gly | Ile | Leu | Ala | Ala | Gly | Arg | Lys | Met | Val |
|     |     |     | 115 |     |     |     |     | 120 |     |     |     |     | 125 |     |     |

| Ala | Leu | Lys | Asn | Pro | Gly | Leu | Ile | Ile | Asn | Thr | Ala | Ser | Val | Tyr | Ala |
|     | 130 |     |     |     |     | 135 |     |     |     |     | 140 |     |     |     |     |

| Phe | Leu | Ala | Ser | Pro | Gly | Val | Ile | Gly | Tyr | His | Ala | Ala | Lys | Gly | Ala |
| 145 |     |     |     |     | 150 |     |     |     |     | 155 |     |     |     |     | 160 |

| Val | Lys | Met | Met | Thr | Gln | Ala | Ala | Ala | Leu | Glu | Leu | Ala | Pro | His | Gly |
|     |     |     |     | 165 |     |     |     |     | 170 |     |     |     |     | 175 |     |

| Ile | Arg | Val | Val | Ala | Ile | Ala | Pro | Gly | Gly | Val | Asp | Thr | Pro | Ile | Ile |
|     |     |     | 180 |     |     |     |     | 185 |     |     |     |     | 190 |     |     |

| Gln | Gly | Tyr | Lys | Asp | Met | Gly | Leu | Gly | Glu | Arg | Leu | Ala | Arg | Gly | Gln |
|     |     |     | 195 |     |     |     |     | 200 |     |     |     |     | 205 |     |     |

| Met | Arg | Arg | Arg | Leu | Gln | Thr | Pro | Glu | Gln | Ile | Ala | Gly | Ala | Val | Ala |
|     | 210 |     |     |     |     | 215 |     |     |     |     | 220 |     |     |     |     |

| Leu | Leu | Ala | Thr | Asp | Glu | Ala | Asp | Ala | Ile | Asn | Gly | Ser | Val | Val | Met |
| 225 |     |     |     |     | 230 |     |     |     |     | 235 |     |     |     |     | 240 |

| Thr | Asp | Asp | Gly | Tyr | Ala | Glu | Phe | Lys |
|     |     |     |     | 245 |     |     |     |     |

<210> SEQ ID NO 3
<211> LENGTH: 243
<212> TYPE: PRT
<213> ORGANISM: Candida magnoliae CBS 6396

<400> SEQUENCE: 3

| Met | Ser | Ala | Thr | Ser | Asn | Ala | Leu | Ile | Thr | Gly | Ala | Ser | Arg | Gly | Met |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gly | Glu | Ala | Thr | Ala | Ile | Lys | Leu | Ala | Leu | Glu | Gly | Tyr | Ser | Val | Thr |
|     |     |     | 20  |     |     |     |     | 25  |     |     |     |     | 30  |     |     |

| Leu | Ala | Ser | Arg | Gly | Ile | Glu | Gln | Leu | Asn | Ala | Ile | Lys | Glu | Lys | Leu |
|     |     |     | 35  |     |     |     |     | 40  |     |     |     |     | 45  |     |     |

| Pro | Ile | Val | Lys | Lys | Gly | Gln | Gln | His | Tyr | Val | Trp | Gln | Leu | Asp | Leu |
|     | 50  |     |     |     |     | 55  |     |     |     |     | 60  |     |     |     |     |

| Ser | Asp | Ile | Glu | Ala | Ala | Ser | Thr | Phe | Lys | Gly | Ala | Pro | Leu | Pro | Ala |
| 65  |     |     |     |     | 70  |     |     |     |     | 75  |     |     |     |     | 80  |

```
Ser Ser Tyr Asp Val Phe Phe Ser Asn Ala Gly Val Asp Phe Ala
             85                  90                  95

Pro Phe Ala Asp Gln Ser Glu Thr Ala Gln Lys Asp Leu Phe Thr Val
        100                 105                 110

Asn Leu Leu Ser Pro Val Ala Leu Thr Lys Thr Ile Val Lys Ala Ile
        115                 120                 125

Ala Asp Lys Pro Arg Glu Thr Pro Ala His Ile Ile Phe Thr Ser Ser
130                 135                 140

Ile Val Gly Ile Arg Gly Val Pro Asn Val Ala Val Tyr Ser Ala Thr
145                 150                 155                 160

Lys Gly Ala Ile Asp Ser Phe Ala Arg Ser Leu Ala Arg Glu Phe Gly
                165                 170                 175

Pro Lys Asn Ile His Val Asn Cys Val Asn Pro Gly Thr Thr Arg Thr
            180                 185                 190

Glu Met Thr Lys Gly Val Asp Leu Ala Ala Phe Gly Asp Val Pro Ile
            195                 200                 205

Lys Gly Trp Ile Glu Val Asp Ala Ile Ala Asp Ala Val Leu Phe Leu
            210                 215                 220

Ile Lys Ser Lys Asn Ile Thr Gly Gln Ser Leu Val Val Asp Asn Gly
225                 230                 235                 240

Phe Gly Val

<210> SEQ ID NO 4
<211> LENGTH: 241
<212> TYPE: PRT
<213> ORGANISM: Candida magnoliae DSM 70638

<400> SEQUENCE: 4

Met Thr Ser Thr Pro Asn Ala Leu Ile Thr Gly Gly Ser Arg Gly Ile
1               5                   10                  15

Gly Ala Ser Ala Ala Ile Lys Leu Ala Gln Glu Gly Tyr Ser Val Thr
            20                  25                  30

Leu Ala Ser Arg Asp Leu Glu Lys Leu Thr Glu Val Lys Asp Lys Leu
        35                  40                  45

Pro Ile Val Arg Gly Gly Gln Lys His Tyr Val Trp Gln Leu Asp Leu
    50                  55                  60

Ala Asp Val Glu Ala Ala Ser Ser Phe Lys Ala Ala Pro Leu Pro Ala
65                  70                  75                  80

Ser Ser Tyr Asp Leu Phe Val Ser Asn Ala Gly Ile Ala Gln Phe Ser
                85                  90                  95

Pro Thr Ala Glu His Thr Asn Ser Glu Trp Leu Asn Ile Met Thr Ile
            100                 105                 110

Asn Leu Val Ser Pro Ile Ala Leu Thr Lys Ala Leu Leu Gln Ala Val
            115                 120                 125

Ser Gly Arg Ser Ser Glu Asn Pro Phe Gln Ile Val Phe Ile Ser Ser
130                 135                 140

Val Ala Ala Leu Arg Gly Val Ala Gln Thr Ala Val Tyr Ser Ala Ser
145                 150                 155                 160

Lys Ala Gly Thr Asp Gly Phe Ala Arg Ser Leu Ala Arg Glu Leu Gly
            165                 170                 175

Pro Gln Gly Val His Val Asn Val Asn Pro Gly Trp Thr Lys Thr
            180                 185                 190

Asp Met Thr Glu Gly Val Glu Thr Pro Lys Asp Met Pro Ile Lys Gly
            195                 200                 205

Trp Ile Gln Pro Glu Ala Ile Ala Asp Ala Val Val Phe Leu Ala Arg
```

```
              210                 215                 220
Ser Lys Asn Ile Thr Gly Ala Asn Ile Val Val Asp Asn Gly Phe Ser
225                 230                 235                 240

Thr

<210> SEQ ID NO 5
<211> LENGTH: 241
<212> TYPE: PRT
<213> ORGANISM: Candida magnoliae DSM 70638

<400> SEQUENCE: 5

Met Thr Thr Thr Ser Asn Ala Leu Val Thr Gly Gly Ser Arg Gly Ile
1               5                   10                  15

Gly Ala Ala Ser Ala Ile Lys Leu Ala Gln Glu Gly Tyr Asn Val Thr
            20                  25                  30

Leu Ala Ser Arg Ser Val Asp Lys Leu Asn Glu Val Lys Ala Lys Leu
        35                  40                  45

Pro Ile Val Gln Asp Gly Gln Lys His Tyr Ile Trp Glu Leu Asp Leu
    50                  55                  60

Ala Asp Val Glu Ala Ala Ser Ser Phe Lys Gly Ala Pro Leu Pro Ala
65                  70                  75                  80

Arg Ser Tyr Asp Val Phe Val Ser Asn Ala Gly Val Ala Ala Phe Ser
                85                  90                  95

Pro Thr Ala Asp His Asp Asp Lys Glu Trp Gln Asn Leu Leu Ala Val
            100                 105                 110

Asn Leu Ser Ser Pro Ile Ala Leu Thr Lys Ala Leu Leu Lys Asp Val
        115                 120                 125

Ser Glu Arg Pro Val Asp Lys Pro Leu Gln Ile Ile Tyr Ile Ser Ser
    130                 135                 140

Val Ala Gly Leu His Gly Ala Ala Gln Val Ala Val Tyr Ser Ala Ser
145                 150                 155                 160

Lys Ala Gly Leu Asp Gly Phe Met Arg Ser Val Ala Arg Glu Val Gly
                165                 170                 175

Pro Lys Gly Ile His Val Asn Ser Ile Asn Pro Gly Tyr Thr Lys Thr
            180                 185                 190

Glu Met Thr Ala Gly Ile Glu Ala Leu Pro Asp Leu Pro Ile Lys Gly
        195                 200                 205

Trp Ile Glu Pro Glu Ala Ile Ala Asp Ala Val Leu Phe Leu Ala Lys
    210                 215                 220

Ser Lys Asn Ile Thr Gly Thr Asn Ile Val Val Asp Asn Gly Leu Ile
225                 230                 235                 240

Ala

<210> SEQ ID NO 6
<211> LENGTH: 759
<212> TYPE: DNA
<213> ORGANISM: Chloroflexus aurantiacus DSM 635

<400> SEQUENCE: 6
atggagccac ctttcattgg aaggttgcg ctggtcaccg gcgcagcagc cggtattggt      60
cgtgcttcag cactggcgtt tgcccgtgag ggtgccaagg ttgtcgttgc tgatgtgaat     120
gtcgagggcg gggaagagac gattgcgctg tgtcgggctt tgaataccga tgcaatgttc    180
gtgcgttgtg atgtttcgca acgcgatgaa gtggagcgat taattgctct ggcagttgac    240
acgttcggtc ggatcgactt tgcgcacaac aacgccggga ttgaaggcgt gcaggcaatg    300
```

-continued

| | |
|---|---|
| ctggccgatt atcccgaaga ggtctgggat cgggtgatcg agatcaacct caaaggggtc | 360 |
| tggttgtgta tgaagtacga aatccggcac atgctcaagc agggtggcgg tgcgattgtg | 420 |
| aatacctcat cggtcgccgg tctggccgga tcacgtggcg tttcggcgta tgtagccagc | 480 |
| aagcacggta ttgttggtat taccaaagcg gcagcccttg agtatgcgcg taacggtatt | 540 |
| cgtgtcaacg caatctgtcc aggtacgatt catactgcga tgatcgaccg ctttacccag | 600 |
| ggtgatcccc aactgcttgc ccagttcgct gagggtgaac cgattggtcg gctcggctcg | 660 |
| cctgaagagg tcgccaatgc ggtgatctgg ctctgctcag ataaggcttc gtttgtgacc | 720 |
| ggagcgacac tggcggttga tggtggccgc ctggcgtaa | 759 |

<210> SEQ ID NO 7
<211> LENGTH: 750
<212> TYPE: DNA
<213> ORGANISM: Rubrobacter xylanophilus DSM 9941

<400> SEQUENCE: 7

| | |
|---|---|
| atgctcgagg ggaaggtcgc ggtcatcacg ggggccggaa gcggcatagg ccgggccacc | 60 |
| gcgctcaagt tcgcccgcga gggggcccgg gtcgtcgccg ccgagctcga cgagcgcggc | 120 |
| ggggaggggg tggtccggga ggtgcgcagc ctcggggggcg aggcggtctt cgtccggacc | 180 |
| gacgtctcgg agttcgcgca ggtggaggac gccgtcgagc gggcggtcgg ggagtacggc | 240 |
| accctcgacg tgatgttcaa caacgccggc atcgggcact acgcccccct gctggagcac | 300 |
| gagcccgagc actacgaccg ggtggtccgg gtgaaccagt acggcgtcta ctacgggata | 360 |
| ctcgccgccg ggagaaagat ggtcgccctg aagaaccccg gcttgatcat caacaccgcc | 420 |
| tcggtctacg ccttcctcgc ctcgccgggg gtcatcggct accacgccgc caaggggcg | 480 |
| gtcaagatga tgacccaggc ggcggcgctg gagctcgccc gcacggcat aagggtcgtc | 540 |
| gccatcgccc cgggcggggt ggacaccccc atcatccagg gctacaagga catggggctc | 600 |
| ggcgagaggc tggcccgcgg ccagatgcgc cgccggctcc agaccccccga gcagatcgcc | 660 |
| ggggcggtcg ccctgctcgc caccgacgag gccgacgcca taaacggctc ggtggtcatg | 720 |
| accgacgacg gctacgcgga gttcaagtag | 750 |

<210> SEQ ID NO 8
<211> LENGTH: 732
<212> TYPE: DNA
<213> ORGANISM: Candida magnoliae CBS 6396

<400> SEQUENCE: 8

| | |
|---|---|
| atgtctgcta cttcgaacgc tcttatcact ggtgccagcc gcggaatggg cgaggccaca | 60 |
| gctattaagc ttgcccttga ggggtacagc gtcacccttg catcacgcgg tattgagcag | 120 |
| ctcaatgcca tcaaggaaaa actacccatc gtgaagaagg ccagcagca ctacgtttgg | 180 |
| cagctcgatc ttagtgacat cgaggcggct tccaccttca agggggctcc tctgcctgcc | 240 |
| agcagctacg acgtgttctt cagcaacgcc ggtgtggtgg actttgctcc gttcgcagac | 300 |
| caaagcgaga ctgcgcaaaa ggacctgttc acggttaacc tgctgtcgcc tgttgcgttg | 360 |
| accaagacca ttgttaaggc catcgccgac aagccccgcg agacgcctgc tcacattatc | 420 |
| ttcacctcgt ccattgtcgg aattcgcggt gttcccaacg tggcggtcta cagcgccacc | 480 |
| aagggcgcga ttgacagctt tgcgcgctcg cttgctcgtg agttcggtcc caagaacatc | 540 |
| cacgttaact gcgtgaaccc gggcacgacg cgcaccgaga tgacaaaggg cgttgatctc | 600 |
| gcggctttcg gcgatgttcc tatcaagggc tggatcgagg tcgatgcgat tgccgacgct | 660 |

```
gtgctgttttt tgatcaagtc caagaacatc actggccagt cgctcgttgt tgacaacgga      720
ttcggtgttt aa                                                           732

<210> SEQ ID NO 9
<211> LENGTH: 726
<212> TYPE: DNA
<213> ORGANISM: Candida magnoliae DSM 70638

<400> SEQUENCE: 9
atgacatcta cacctaatgc cctcatcacg ggaggcagcc gcggcattgg cgcttccgcc       60
gccatcaaac tggctcaaga agggtacagc gtcacgctgg cgtcccgcga ccttgagaaa      120
cttactgagg tcaaggacaa gctgccaatc gtgagaggtg acagaaaaca ctacgtttgg      180
cagctcgatc ttgccgatgt ggaggctgca tcgtctttca aggcggctcc tctgccggcc      240
agcagctacg atttgtttgt tcgaacgcc ggaattgccc agttctcgcc tacggcagag       300
catactaata gtgagtggct gaacattatg accattaact tagtgtcccc gattgccctg      360
acgaaggctc ttttgcaggc cgtttctggg aggtcgagcg agaacccgtt tcagatcgtc      420
ttcatctcgt cggttgcagc actacgtggc gttgcacaaa cggccgtcta cagtgcgtcg      480
aaggctggta ctgatggatt cgcacgctca cttgctcgcg aactaggtcc tcaaggtgtt      540
catgtgaacg tggtgaaccc tggctggact aagacagaca tgacggaagg agtcgaaacc      600
ccaaaggaca tgcccattaa gggctggatc cagcctgagg caattgctga tgctgtagta      660
ttccttgcga ggtcgaaaaa cattaccggc gcgaatattg tagtggacaa tggtttctcg      720
acgtaa                                                                 726

<210> SEQ ID NO 10
<211> LENGTH: 726
<212> TYPE: DNA
<213> ORGANISM: Candida magnoliae DSM 70638

<400> SEQUENCE: 10
atgacgacta cttcaaacgc gcttgtcact ggaggcagcc gcggcattgg cgctgcctcc       60
gccattaagc tggctcagga gggctacaat gttacgctgg cctctcgcag tgttgataaa      120
ctgaatgaag taaaggcgaa actcccaatt gtacaggacg ggcagaagca ctacatttgg      180
gaactcgatc tggctgatgt ggaagctgct tcgtcgttca agggtgctcc tttgcctgct      240
cgcagctacg acgtctttgt tcgaacgcg ggcgtcgctg cgttctcgcc cacagccgac       300
cacgatgata aggagtggca gaacttgctt gccgtgaact tgtcgtcgcc cattgccctc      360
acgaaggccc tcttgaagga tgtctccgaa aggcctgtgg acaagccact gcagattatc      420
tacatttcgt cggtggccgg cttgcatggc gccgcgcagg tcgccgtgta cagtgcatct      480
aaggccggtc ttgatggttt tatgcgctcc gtcgcccgtg aggtgggccc gaagggcatc      540
catgtgaact ccatcaaccc cggatacacg aagactgaaa tgaccgcggg cattgaagcc      600
cttcctgatt tgcctatcaa ggggtggatc gagcccgagg caattgctga cgcggttctg      660
tttctggcaa agtccaagaa tatcaccggc acaaacattg tggtcgacaa tggcttgatt      720
gcttaa                                                                 726

<210> SEQ ID NO 11
<211> LENGTH: 38
<212> TYPE: DNA
<213> ORGANISM: Artificial Sequence
<220> FEATURE:
<221> NAME/KEY: misc_feature
<222> LOCATION: (1)..(38)
```

<223> OTHER INFORMATION: primer

<400> SEQUENCE: 11
ggaattccat atgatggagc cacctttcat tgggaagg                              38

<210> SEQ ID NO 12
<211> LENGTH: 34
<212> TYPE: DNA
<213> ORGANISM: Artificial Sequence
<220> FEATURE:
<221> NAME/KEY: misc_feature
<222> LOCATION: (1)..(34)
<223> OTHER INFORMATION: primer

<400> SEQUENCE: 12
cccaagctta ttattacgcc aggcggccac catc                                  34

<210> SEQ ID NO 13
<211> LENGTH: 34
<212> TYPE: DNA
<213> ORGANISM: Artificial Sequence
<220> FEATURE:
<221> NAME/KEY: misc_feature
<222> LOCATION: (1)..(34)
<223> OTHER INFORMATION: primer

<400> SEQUENCE: 13
cccaagctta ttattacgcc aggcggccac catc                                  34

<210> SEQ ID NO 14
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: primer

<400> SEQUENCE: 14
ggaattccat atgatgtctg ctacttcgaa cgctc                                 35

<210> SEQ ID NO 15
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: primer

<400> SEQUENCE: 15
ccgctcgagt tattaaacac cgaatccgtt gtc                                   33

<210> SEQ ID NO 16
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: primer

<400> SEQUENCE: 16
cacatgcatg cagatgtctg ctacttcgaa cgctc                                 35

<210> SEQ ID NO 17
<211> LENGTH: 34
<212> TYPE: DNA

<213> ORGANISM: Artificial Sequence
<220> FEATURE:
<221> NAME/KEY: misc_feature
<222> LOCATION: (1)..(34)
<223> OTHER INFORMATION: primer

<400> SEQUENCE: 17
gcccgagctc ttattaaaca ccgaatccgt tgtc                        34

<210> SEQ ID NO 18
<211> LENGTH: 12
<212> TYPE: PRT
<213> ORGANISM: Artificial Sequence
<220> FEATURE:
<221> NAME/KEY: misc_feature
<222> LOCATION: (1)..(12)
<223> OTHER INFORMATION: partial sequence ofoxidoreductase/dehydrogenase

<400> SEQUENCE: 18

Asn Ala Leu Val Thr Gly Ala Ser Arg Gly Ile Gly
1               5                   10

<210> SEQ ID NO 19
<211> LENGTH: 12
<212> TYPE: PRT
<213> ORGANISM: Artificial Sequence
<220> FEATURE:
<221> NAME/KEY: misc_feature
<222> LOCATION: (1)..(12)
<223> OTHER INFORMATION: partial sequence ofoxidoreductase/dehydrogenase

<400> SEQUENCE: 19

Asn Ala Leu Val Thr Gly Gly Ser Arg Gly Ile Gly
1               5                   10

<210> SEQ ID NO 20
<211> LENGTH: 12
<212> TYPE: PRT
<213> ORGANISM: Artificial Sequence
<220> FEATURE:
<221> NAME/KEY: misc_feature
<222> LOCATION: (1)..(12)
<223> OTHER INFORMATION: partial sequence ofoxidoreductase/dehydrogenase

<400> SEQUENCE: 20

Asn Ala Leu Ile Thr Gly Gly Ser Arg Gly Ile Gly
1               5                   10

<210> SEQ ID NO 21
<211> LENGTH: 12
<212> TYPE: PRT
<213> ORGANISM: Artificial Sequence
<220> FEATURE:
<221> NAME/KEY: misc_feature
<222> LOCATION: (1)..(12)
<223> OTHER INFORMATION: partial sequence ofoxidoreductase/dehydrogenase

<400> SEQUENCE: 21

Asn Ala Leu Ile Thr Gly Ala Ser Arg Gly Ile Gly
1               5                   10

<210> SEQ ID NO 22
<211> LENGTH: 12
<212> TYPE: PRT
<213> ORGANISM: Artificial Sequence
<220> FEATURE:
<221> NAME/KEY: misc_feature
<222> LOCATION: (1)..(12)
<223> OTHER INFORMATION: partial sequence ofoxidoreductase/dehydrogenase

```
<400> SEQUENCE: 22

Asn Ala Leu Ile Thr Gly Gly Ser Arg Gly Met Gly
1               5                   10

<210> SEQ ID NO 23
<211> LENGTH: 12
<212> TYPE: PRT
<213> ORGANISM: Artificial Sequence
<220> FEATURE:
<221> NAME/KEY: misc_feature
<222> LOCATION: (1)..(12)
<223> OTHER INFORMATION: partial sequence ofoxidoreductase/dehydrogenase

<400> SEQUENCE: 23

His Ala Leu Val Thr Gly Ala Ser Arg Gly Ile Gly
1               5                   10

<210> SEQ ID NO 24
<211> LENGTH: 7
<212> TYPE: PRT
<213> ORGANISM: Artificial Sequence
<220> FEATURE:
<221> NAME/KEY: misc_feature
<222> LOCATION: (1)..(7)
<223> OTHER INFORMATION: partial sequence ofoxidoreductase/dehydrogenase

<400> SEQUENCE: 24

Gly Tyr Ser Val Thr Leu Ala
1               5

<210> SEQ ID NO 25
<211> LENGTH: 7
<212> TYPE: PRT
<213> ORGANISM: Artificial Sequence
<220> FEATURE:
<221> NAME/KEY: misc_feature
<222> LOCATION: (1)..(7)
<223> OTHER INFORMATION: partial sequence ofoxidoreductase/dehydrogenase

<400> SEQUENCE: 25

Gly Tyr Asn Val Thr Leu Ala
1               5

<210> SEQ ID NO 26
<211> LENGTH: 7
<212> TYPE: PRT
<213> ORGANISM: Artificial Sequence
<220> FEATURE:
<221> NAME/KEY: misc_feature
<222> LOCATION: (1)..(7)
<223> OTHER INFORMATION: partial sequence ofoxidoreductase/dehydrogenase

<400> SEQUENCE: 26

Gly Tyr Ser Val Thr Leu Val
1               5

<210> SEQ ID NO 27
<211> LENGTH: 7
<212> TYPE: PRT
<213> ORGANISM: Artificial Sequence
<220> FEATURE:
<221> NAME/KEY: misc_feature
<222> LOCATION: (1)..(7)
<223> OTHER INFORMATION: partial sequence ofoxidoreductase/dehydrogenase

<400> SEQUENCE: 27

Gly Tyr Asn Val Thr Leu Val
1               5
```

```
<210> SEQ ID NO 28
<211> LENGTH: 8
<212> TYPE: PRT
<213> ORGANISM: Artificial Sequence
<220> FEATURE:
<221> NAME/KEY: misc_feature
<222> LOCATION: (1)..(8)
<223> OTHER INFORMATION: partial sequence ofoxidoreductase/dehydrogenase

<400> SEQUENCE: 28

Phe Lys Gly Ala Pro Leu Pro Ala
1               5

<210> SEQ ID NO 29
<211> LENGTH: 8
<212> TYPE: PRT
<213> ORGANISM: Artificial Sequence
<220> FEATURE:
<221> NAME/KEY: misc_feature
<222> LOCATION: (1)..(8)
<223> OTHER INFORMATION: partial sequence ofoxidoreductase/dehydrogenase

<400> SEQUENCE: 29

Phe Lys Ala Ala Pro Leu Pro Ala
1               5

<210> SEQ ID NO 30
<211> LENGTH: 6
<212> TYPE: PRT
<213> ORGANISM: Artificial Sequence
<220> FEATURE:
<221> NAME/KEY: misc_feature
<222> LOCATION: (1)..(6)
<223> OTHER INFORMATION: partial sequence ofoxidoreductase/dehydrogenase

<400> SEQUENCE: 30

Phe Val Ser Asn Ala Gly
1               5

<210> SEQ ID NO 31
<211> LENGTH: 6
<212> TYPE: PRT
<213> ORGANISM: Artificial Sequence
<220> FEATURE:
<221> NAME/KEY: misc_feature
<222> LOCATION: (1)..(6)
<223> OTHER INFORMATION: partial sequence ofoxidoreductase/dehydrogenase

<400> SEQUENCE: 31

Phe Phe Ser Asn Ala Gly
1               5

<210> SEQ ID NO 32
<211> LENGTH: 6
<212> TYPE: PRT
<213> ORGANISM: Artificial Sequence
<220> FEATURE:
<221> NAME/KEY: misc_feature
<222> LOCATION: (1)..(6)
<223> OTHER INFORMATION: partial sequence ofoxidoreductase/dehydrogenase

<400> SEQUENCE: 32

Phe Val Cys Asn Ala Gly
1               5

<210> SEQ ID NO 33
<211> LENGTH: 6
<212> TYPE: PRT
<213> ORGANISM: Artificial Sequence
```

```
<220> FEATURE:
<221> NAME/KEY: misc_feature
<222> LOCATION: (1)..(6)
<223> OTHER INFORMATION: partial sequence ofoxidoreductase/dehydrogenase

<400> SEQUENCE: 33

Phe Val Ala Asn Ala Gly
1               5

<210> SEQ ID NO 34
<211> LENGTH: 9
<212> TYPE: PRT
<213> ORGANISM: Artificial Sequence
<220> FEATURE:
<221> NAME/KEY: misc_feature
<222> LOCATION: (1)..(9)
<223> OTHER INFORMATION: partial sequence ofoxidoreductase/dehydrogenase

<400> SEQUENCE: 34

Ser Pro Ile Ala Leu Thr Lys Ala Leu
1               5

<210> SEQ ID NO 35
<211> LENGTH: 9
<212> TYPE: PRT
<213> ORGANISM: Artificial Sequence
<220> FEATURE:
<221> NAME/KEY: misc_feature
<222> LOCATION: (1)..(9)
<223> OTHER INFORMATION: partial sequence ofoxidoreductase/dehydrogenase

<400> SEQUENCE: 35

Ser Pro Val Ala Leu Thr Lys Thr Ile
1               5

<210> SEQ ID NO 36
<211> LENGTH: 9
<212> TYPE: PRT
<213> ORGANISM: Artificial Sequence
<220> FEATURE:
<221> NAME/KEY: misc_feature
<222> LOCATION: (1)..(9)
<223> OTHER INFORMATION: partial sequence ofoxidoreductase/dehydrogenase

<400> SEQUENCE: 36

Ser Pro Ile Ala Leu Thr Lys Thr Leu
1               5

<210> SEQ ID NO 37
<211> LENGTH: 9
<212> TYPE: PRT
<213> ORGANISM: Artificial Sequence
<220> FEATURE:
<221> NAME/KEY: misc_feature
<222> LOCATION: (1)..(9)
<223> OTHER INFORMATION: partial sequence ofoxidoreductase/dehydrogenase

<400> SEQUENCE: 37

Ser Pro Val Ala Met Thr Lys Ala Leu
1               5

<210> SEQ ID NO 38
<211> LENGTH: 9
<212> TYPE: PRT
<213> ORGANISM: Artificial Sequence
<220> FEATURE:
<221> NAME/KEY: misc_feature
<222> LOCATION: (1)..(9)
<223> OTHER INFORMATION: partial sequence ofoxidoreductase/dehydrogenase
```

```
<400> SEQUENCE: 38

Ser Gln Ile Ala Leu Thr Lys Ala Leu
1               5

<210> SEQ ID NO 39
<211> LENGTH: 7
<212> TYPE: PRT
<213> ORGANISM: Artificial Sequence
<220> FEATURE:
<221> NAME/KEY: misc_feature
<222> LOCATION: (1)..(7)
<223> OTHER INFORMATION: partial sequence ofoxidoreductase/dehydrogenase

<400> SEQUENCE: 39

Ala Val Tyr Ser Ala Ser Lys
1               5

<210> SEQ ID NO 40
<211> LENGTH: 7
<212> TYPE: PRT
<213> ORGANISM: Artificial Sequence
<220> FEATURE:
<221> NAME/KEY: misc_feature
<222> LOCATION: (1)..(7)
<223> OTHER INFORMATION: partial sequence ofoxidoreductase/dehydrogenase

<400> SEQUENCE: 40

Ala Val Tyr Ser Ala Thr Lys
1               5

<210> SEQ ID NO 41
<211> LENGTH: 6
<212> TYPE: PRT
<213> ORGANISM: Artificial Sequence
<220> FEATURE:
<221> NAME/KEY: misc_feature
<222> LOCATION: (1)..(6)
<223> OTHER INFORMATION: partial sequence ofoxidoreductase/dehydrogenase

<400> SEQUENCE: 41

Pro Ile Lys Gly Trp Ile
1               5

<210> SEQ ID NO 42
<211> LENGTH: 6
<212> TYPE: PRT
<213> ORGANISM: Artificial Sequence
<220> FEATURE:
<221> NAME/KEY: misc_feature
<222> LOCATION: (1)..(6)
<223> OTHER INFORMATION: partial sequence ofoxidoreductase/dehydrogenase

<400> SEQUENCE: 42

Pro Ile Ser Gly Trp Ile
1               5
```

PROCESS FOR THE ENANTIOSELECTIVE ENZYMATIC REDUCTION OF SECODIONE DERIVATIVES

CROSS REFERENCE TO RELATED APPLICATIONS

The present application is a continuation of U.S. patent application Ser. No. 12/518,025, filed Jul. 6, 2009, which is a United States Nationalization of International Application No. PCT/EP2007/010640 filed Dec. 7, 2007, which claims priority to Austrian Application No. A 2027/2006, filed Dec. 7, 2006, each of the proceeding are incorporated herein by reference in their entireties.

The present invention relates to a process for the enantioselective enzymatic reduction of secodione derivatives of general formula I, wherein the secodione derivative is reduced with an oxidoreductase/dehydrogenase in the presence of NADH or NADPH as a cofactor.

The industrial preparation of steroid hormones occurs in two ways which are independent of each other, namely, on the one hand, starting out from naturally occurring steriod compounds from plant sources and, on the other hand, in a totally synthetic manner via an enantioselective synthesis from prochiral precursors. Among those two ways, the steroid total synthesis is increasingly gaining in importance, particularly since it also allows the introduction of structural elements which are not contained in naturally occurring steriods.

Key components of the total synthesis of enantiomerically pure steriods are thereby compounds of general formula I, which are also referred to as secosteroids, 8,14-seco-gona-tetraene-14,17-diones or secodiones. Specific representatives of this group are, for example, the compounds methyl secodione (Formula II, 13-methyl-3-methoxy-8,14-seco-gona-1,3,5(10),9(11)-tetraene-14,17-dione) and ethyl secodione (Formula III, 13-ethyl-3-methoxy-8,14-seco-gona-1,3,5(10),9(11)-tetraene-14,17-dione), from which, for example, the pharmacologically active compounds ethinyl estradiol (Formula IV) and norgestrel (Formula V) can be produced.

Formula II

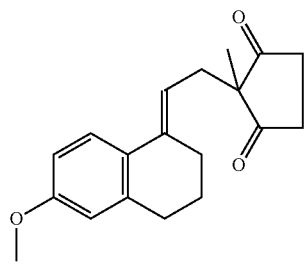

Formula III

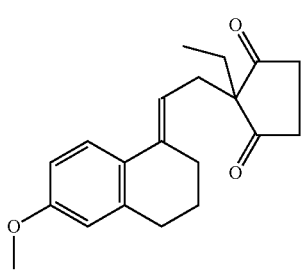

Formula IV

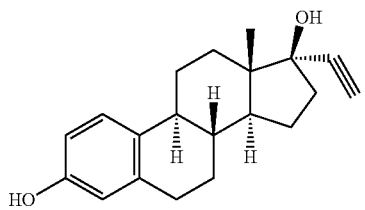

Formula V

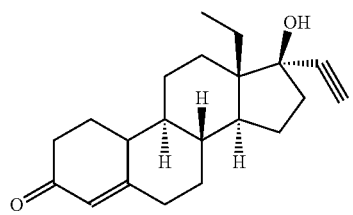

A key step in the preparation of enantiomerically pure steroid compounds is the conversion of the compound of formula I (e.g., II and III) into an optically active compound with a preformed asymmetric C-13 by enantioselective reduction of one of the keto groups to the hydroxy group. The resulting optically active hydroxy secosteroid compounds (secoles, Formulae VI to IX) can subsequently be processed further into chiral steroid compounds by cyclization, while chirality is maintained.

By enantioselective reduction of a keto group of the compound of formula I, four optically active compounds can, in theory, be formed (Formulae VI to IX).

Formula VI

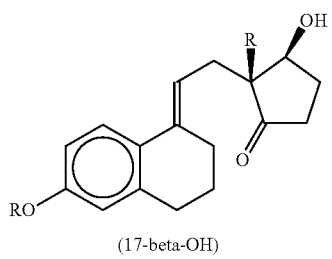

(17-beta-OH)

Formula VII

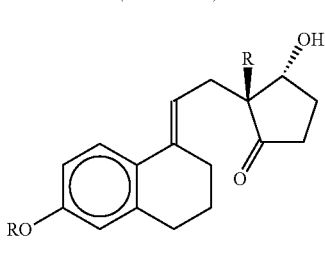

(17-alpha-OH)

Formula VIII

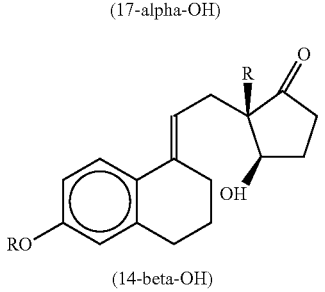

(14-beta-OH)

-continued

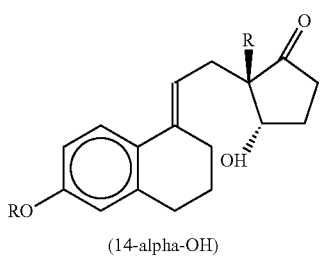

Formula IX (14-alpha-OH)

Compounds of formula VI, in which the hydroxy group exhibits the beta-configuration at position 17, are thereby of particular economic interest, since they result in derivatives of the natural estrone. Such compounds are also referred to as 17-beta-hydroxy secosteroids.

The stereoselective reduction of secodione derivatives of general formula I with the aid of different microorganisms was examined particularly thoroughly in the 60ies and 70ies. In doing so, it could be shown that different yeast strains of the genera *Candida, Debaryomyces, Kloeckera, Pichia, Cryptococcus, Rhodotorula, Torulopsis* and *Hansenula* are capable of reducing secodiones to various hydroxy compounds (U.S. Pat. Nos. 3,616,226, 1,252,524, 3,616,225).

In particular, yeasts of the genus *Saccharomyces* such as, e.g., *S. uvarum* can be used advantageously for preparing, for example, the respective 17-beta-hydroxy secosteroids (Kosmol et al; Liebigs Ann. Chem. 701,199 (1967)). Other yeast strains such as, e.g., *Saccharomyces drosophilarum* reduce secodione preferably to the corresponding 14-alpha-hydroxy secosteroid (Acta microbiol. Acad. Sci. hung. 22, 463-471 (1975)). Furthermore, the formation of 14-alpha-hydroxy secosteroid is also described by the reduction of secodione by means of *Bacillus thuringiensis* (Kosmol et al.; Liebigs Ann Chem. 701,199 (1967)).

Gestagen and estrogen agents are widely used all over the world as contraceptives and in hormone replacement therapy. Most syntheses of estrogen and gestagen derivatives have to date been based on the above-described reaction principle, the key step of which is the enantioselective reduction of secodiones to the corresponding 17-beta-hydroxy secosteroids.

In doing so, the stereoselective reduction of secodione derivatives has to date been performed as a whole-cell biotransformation using different yeast strains of the genus *Pichia* or *Saccharomyces*. However, those processes have the disadvantage that only very low substrate concentrations of far below 1% (normally from 1 to 5 g/l) are feasible (U.S. Pat. No. 3,697,379; Current Science, Feb. 5 (1984), Vol 53. No. 3, p. 124; Indian Journal of Experimental Biology, Vol. 27, August 1989, p. 742-743). Thus, in particular the reprocessing and isolation of the reaction product from large volumes as well as the separation of large amounts of biomass turn out to be very complex. To the inventors' knowledge, the enzymes involved in the reduction have so far not been isolated, identified and described. Likewise, DNA sequences which code for oxidoreductases by means of which the reduction of secodione derivatives can be achieved have not yet been identified.

Thus, it is the object of the invention to provide a process by means of which secodione derivatives of general formula I, particularly those of formulae II and III, can be reduced enantioselectively. In this way, among other things, also the production of the corresponding 17-beta-hydroxy secosteroids should be rendered feasible.

In a first aspect, said object is achieved according to the invention by a process for the enantioselective enzymatic reduction of secodione derivatives of general formula I,

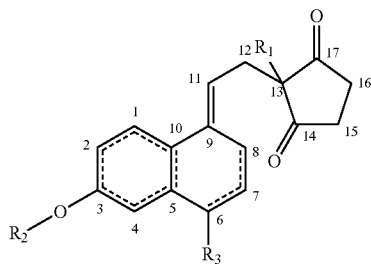

(I)

wherein the ring structures comprise no, one or several heteroatoms,
R1 is hydrogen or a C1-C4 alkyl group,
R2 is hydrogen, a C1-C8 alkyl group or a protective group for OH known in prior art, such as an ester,
R3 is hydrogen, a methyl group or a halide,
the structural element

represents a benzene ring or a C6 ring having 0, 1 or 2 C—C double bonds,
a double bond is optionally included at positions 6/7 or 7/8, and
the carbon at positions 1, 2, 4, 5, 6, 7, 8, 9, 11, 12 and 16 is independently substituted with hydrogen, a C1-C4 alkyl group, a halide or a phenyl group,
wherein the secodione derivative is reduced with an oxidoreductase/dehydrogenase in the presence of NADH or NADPH as a cofactor,
which process is characterized in that the secodione derivative is used in the reaction batch at a concentration of ≧10 g/l and the oxidized cofactor NAD or NADP formed by the oxidoreductase/dehydrogenase is regenerated continuously.

This process represents a significant improvement of the enantioselective enzymatic reduction of secodione derivatives over the prior art. The process according to the invention allows the reduction of secodione derivatives to the different corresponding hydroxy secosteroids with free enzymes at concentration ranges far exceeding those described in the prior art.

In a second aspect, the above-mentioned object is achieved according to the invention by a process for the enantioselective enzymatic reduction of secodione derivatives of general formula I, wherein the secodione derivative is reduced with an oxidoreductase/dehydrogenase in the presence of NADH or NADPH as a cofactor, which process is characterized in that the oxidoreductase/dehydrogenase
a) comprises an amino acid sequence in which at least 50% of the amino acids are identical to those of amino acid sequence SEQ ID NO:1, SEQ ID NO:2, SEQ ID NO:3, SEQ ID NO:4 or SEQ ID NO:5,
b) is encoded by the nucleic acid sequence SEQ ID NO:6, SEQ ID NO:7, SEQ ID NO:8, SEQ ID NO:9 or SEQ ID NO:10, or c) is encoded by a nucleic acid sequence which hybridizes to SEQ ID NO:6, SEQ ID NO:7, SEQ ID NO:8, SEQ ID NO:9 or SEQ ID NO:10 under stringent conditions.

The inventors have identified oxidoreductases which are capable of reducing secodione derivatives to hydroxy secosteroids and which can be produced recombinantly on an industrial scale. Significantly higher substrate concentrations can be achieved by the process according to the invention than with the currently used whole-cell processes.

In the process according to the invention, the oxidoreductase having the sequence SEQ ID NO:1, SEQ ID NO:2, SEQ ID NO:3, SEQ ID NO:4 or SEQ ID NO:5 or a polypeptide derivable from those polypeptides, respectively, can be used either in a completely purified state, in a partially purified state or as cells containing the polypeptide SEQ ID NO:1, SEQ ID NO:2, SEQ ID NO:3, SEQ ID NO:4 or SEQ ID NO:5. Thereby, the cells used can be provided in a native, permeabilized or lysed state. Preferably, the oxidoreductases and derivatives derivable therefrom, respectively, are overexpressed in a suitable host organism such as, e.g., *Escherichia coli*, and the recombinant polypeptide is used for the reduction of secodione derivatives of general formula I.

A DNA sequence SEQ ID NO:6 which codes for a polypeptide with SEQ ID NO:1 is obtainable, for example, from the genome of the organism *Chloroflexus aurantiacus* DSM 635.

A DNA sequence SEQ ID NO:7 which codes for a polypeptide with SEQ ID NO:2 is obtainable, for example, from the genome of the organism *Rubrobacter xylanophilus* DSM 9941.

A DNA sequence SEQ ID NO:8 which codes for a polypeptide with SEQ ID NO:3 is obtainable from a yeast *Candida magnoliae* CBS 6396.

Oxidoreductases of SEQ ID NO:4 and SEQ ID NO:5 are obtainable, for example, from *Candida magnoliae* DSMZ 70638 by homology screening.

A nucleic acid sequence which hybridizes, for example, to SEQ ID NO:6 under stringent conditions is understood to be a polynucleotide which can be identified via the colony hybridization method, the plaque hybridization method, the Southern hybridization method or comparable methods, using SEQ ID NO:6 or partial sequences of SEQ ID NO:6 as a DNA probe. For this purpose, the polynucleotide immobilized on a filter is hybridized, for example, to SEQ ID NO:6 in a 0.7-1 M NaCl solution at 60° C. Hybridization is carried out as described, e.g., in Molecular Cloning, A Laboratory Manual, Second Edition (Cold Spring Harbor Laboratory Press, 1989) or in similar publications. Subsequently, the filter is washed with a 0.1 to 2-fold SSC solution at 65° C., wherein a 1-fold SSC solution is understood to be a mixture consisting of 150 mM NaCl and 15 mM sodium citrate.

A polynucleotide which hybridizes to the polynucleotides SEQ ID NO:6, SEQ ID NO:7, SEQ ID NO:8, SEQ ID NO:9 or SEQ ID NO:10 from the sequence list under the above-mentioned stringent conditions should exhibit at least 60% sequence identity to the polynucleotide sequences SEQ ID NO:6, SEQ ID NO:7, SEQ ID NO:8, SEQ ID NO:9 or SEQ ID NO:10, better an identity of at least 80%, even better an identity of 95%.

In a further aspect, the above-mentioned object is achieved according to the invention by a process for the enantioselective enzymatic reduction of secodione derivatives of general formula I, wherein the secodione derivative is reduced with an oxidoreductase/dehydrogenase in the presence of NADH or NADPH as a cofactor, which process is characterized in that the oxidoreductase/dehydrogenase has a length of from 230 to 260 amino acids and comprises one or several of the partial sequences selected from the group consisting of [sequences SEQ ID NO:18 to SEQ ID NO:42]
nalvtgasrgig, nalvtggsrgig, nalitggsrgig, nalitgasrgig, nalitggsrgmg, halvtgasrgig,
gysvtla, gynvtla, gysvtiv, gynvtiv,
fkgaplpa, fkaaplpa,
fvsnag, ffsnag, fvcnag, fvanag,
spialtkal, spvaltkti, spialtktl, spvamtkal, sqialtkal,
avysask, avysatk,
pikgwi and pisgwi.

In the processes according to the invention, NADH or NADPH is used as the cofactor. By the term "NADP", nicotinamide adenine dinucleotide phosphate is understood, by "NADPH", reduced nicotinamide adenine dinucleotide phosphate is understood. The term "NAD" means nicotinamide adenine dinucleotide, the term "NADH" means reduced nicotinamide adenine dinucleotide.

According to a preferred embodiment of the process in which the secodione derivative is used in the reaction batch at a concentration of $\geqq 10$ g/l and the oxidized cofactor NAD or NADP formed by the oxidoreductase/dehydrogenase is regenerated continuously, the oxidoreductase/dehydrogenase
a) comprises an amino acid sequence in which at least 50% of the amino acids are identical to those of amino acid sequence SEQ ID NO:1, SEQ ID NO:2, SEQ ID NO:3, SEQ ID NO:4 or SEQ ID NO:5,
b) the oxidoreductase/dehydrogenase is encoded by the nucleic acid sequence SEQ ID NO:6, SEQ ID NO:7, SEQ ID NO:8, SEQ ID NO:9 or SEQ ID NO:10, or
c) the oxidoreductase/dehydrogenase is encoded by a nucleic acid sequence which hybridizes to SEQ ID NO:6, SEQ ID NO:7, SEQ ID NO:8, SEQ ID NO:9 or SEQ ID NO:10 under stringent conditions.

According to another preferred embodiment of the process in which the secodione derivative is used in the reaction batch at a concentration of $\geqq 10$ g/l and the oxidized cofactor NAD or NADP formed by the oxidoreductase/dehydrogenase is regenerated continuously, the oxidoreductase/dehydrogenase has a length of from 230 to 260 amino acids and comprises one or several of the partial sequences selected from the group consisting of [sequences SEQ ID NO:18 to SEQ ID NO:42]
nalvtgasrgig, nalvtggsrgig, nalitggsrgig, nalitgasrgig, nalitggsrgmg, halvtgasrgig, gysvtla, gynvtla, gysvtiv, gynvtiv, fkgaplpa, fkaaplpa, fvsnag, ffsnag, fvcnag, fvanag, spialtkal, spvaltkti, spialtktl, spvamtkal, sqialtkal, avysask, avysatk, pikgwi and pisgwi.

In the processes according to the invention, which refer to the second and third aspects of the invention, the oxidized cofactor NAD or NADP formed by the oxidoreductase/dehydrogenase is preferably regenerated continuously.

According to a preferred embodiment of all processes according to the invention, the oxidized cofactor NAD or NADP is regenerated by oxidation of an alcohol.

In doing so, primary and secondary alcohols such as ethanol, 2-propanol, 2-butanol, 2-pentanol, 3-pentanol, 4-methyl-2-pentanol, 2-hexanol, 2-heptanol, 2-octanol or cyclohexanol are preferably used as cosubstrates. The proportion of the cosubstrate for the regeneration may range from 5 to 95% by volume, based on the total volume.

A secondary alcohol having the general formula $R_X R_Y$-CHOH is preferably used for cofactor regeneration, wherein $R_X$ and $R_Y$ independently of each other are hydrogen, a branched or unbranched $C_1$-$C_8$ alkyl group and $C_{total} \geqq 3$.

According to another preferred embodiment of the processes according to the invention, an oxidoreductase/dehydrogenase is additionally added for the regeneration of the cofactor.

Suitable NADH-dependent alcohol dehydrogenases are, for example, obtainable from baker's yeast, from *Candida parapsilosis* (CPCR) (U.S. Pat. Nos. 5,523,223 and 5,763, 236, Enzyme Microb. Technol., 1993, 15(11):950-8), *Pichia capsulata* (DE 10327454.4), from *Rhodococcus erythropolis* (RECR) (U.S. Pat. No. 5,523,223), *Norcardia fusca* (Biosci. Biotechnol. Biochem., 63(10), 1999, p. 1721-1729; Appl. Microbiol. Biotechnol, 2003, 62(4):380-6; Epub 2003, Apr. 26) or *Rhodococcus ruber* (J. Org. Chem., 2003, 68(2):402-6). Suitable cosubstrates for those alcohol dehydrogenases are, for example, the already mentioned secondary alcohols such as 2-propanol (isopropanol), 2-butanol, 2-pentanol, 4-methyl-2-pentanol, 2-octanol or cyclohexanol.

Suitable secondary alcohol dehydrogenases for the regeneration of NADPH are, for example, those as described above and isolated from organisms of the order of Lactobacillales, e.g., *Lactobacillus kefir* (U.S. Pat. No. 5,200,335), *Lactobacillus brevis* (DE 19610984 A1; Acta Crystallogr. D. Biol. Crystallogr. 2000 December; 56 Pt 12:1696-8), *Lactobacillus minor* (DE 10119274), *Leuconostoc carnosum* (A 1261/ 2005, K1. C12N) or, as described, those from *Thermoanerobium brockii, Thermoanerobium ethanolicus* or *Clostridium beijerinckii*.

However, other enzymatic systems can, in principle, also be used for cofactor regeneration. For example, cofactor regeneration can be effected using NAD- or NADP-dependent formate dehydrogenase (Tishkov et al., J. Biotechnol. Bioeng. [1999] 64, 187-193, Pilot-scale production and isolation of recombinant NAD and NADP specific formate dehydrogenase). Suitable cosubstrates of formate dehydrogenase are, for example, salts of formic acid such as ammonium formate, sodium formate or calcium formate.

The TTN (total turn over number=mol of reduced secodione compound/mol of cofactor used) achieved in the processes according to the invention normally ranges from $10^2$ to $10^5$, preferably, however, it is $\geq 10^3$.

According to a preferred embodiment, the processes according to the invention are carried out in an aqueous organic two-phase system.

Accordingly, the conversion of the secodione derivative occurs in a two-phase system containing, for example, a 2-alcohol for cofactor regeneration, an oxidoreductase, water, cofactor and the secodione compound. However, additional organic solvents which are not involved in the cofactor regeneration, i.e., do not contain any oxidizable hydroxy groups, can also be included. Diethyl ether, tertiary butyl methyl ether, diisopropyl ether, dibutyl ether, ethyl acetate, butyl acetate, heptane, hexane, toluene, dichloromethane, cyclohexane or mixtures thereof are preferably used as additional organic solvents.

Thereby, the amount of non-water-miscible organic components of the two-phase system may range from 10% to 90%, preferably from 20% to 80%, based on the total volume of the reaction batch. The aqueous amount may range from 90% to 10%, preferably from 80% to 20%, based on the total volume of the reaction batch.

A buffer can also be added to the water, for example, a potassium phosphate, tris/HCl, glycine or triethanolamine buffer, having a pH value of from 5 to 10, preferably from 6 to 9. In addition, the buffer can comprise ions for stabilizing or activating both enzymes, for example, magnesium ions or zinc ions.

Moreover, further additives for stabilizing the enzymes used can be used in the processes according to the invention, for example, glycerol, sorbitol, 1,4-DL-dithiothreitol (DTT) or dimethyl sulfoxide (DMSO).

The concentration of the cofactor NAD(P)H, based on the aqueous phase, ranges from 0.001 mM to 10 mM, in particular from 0.01 mM to 1.0 mM. Depending on the specific properties of the enzymes used, the temperature can be from 10° C. to 70° C., preferably from 20° C. to 35° C.

Normally, the secodione derivatives to be reduced are poorly soluble in water. Therefore, the substrate can be provided in a completely or also incompletely dissolved state during the reaction. If the substrate is not dissolved completely in the reaction mixture, a portion of the substrate is present in a solid form and can thus form a third solid phase. The reaction mixture may also temporarily form an emulsion during the conversion.

In the processes according to the invention, the secodione derivative of general formula I is used in the reaction batch preferably in an amount of from 10 g/l to 500 g/l, preferably from 25 g/l to 300 g/l, particularly preferably from 50 g/l to 200 g/l, based on the total volume.

Preferred embodiments of the invention are furthermore characterized in that 13-ethyl-3-methoxy-8,14-seco-gona-1, 3,5(10),9(11)-tetraene-14,17-dione (ethyl secodione—Formula III) or 13-methyl-3-methoxy-8,14-seco-gona-1,3,5 (10),9(11)-tetraene-14,17-dione (methyl secodione—Formula II) is used as the secodione derivative.

The processes according to the invention are carried out, for example, in a reaction vessel made of glass or metal. For this purpose, the components are transferred individually into the reaction vessel and stirred under an atmosphere of, e.g., nitrogen or air. The reaction time ranges from one hour to 7 days, in particular from 2 hours to 48 hours, depending on the secodione compound and the oxidoreductase used. During that time, the secodione compound is reduced to the corresponding hydroxy secosteroid compound by at least 50%.

Below, the present invention is illustrated in more detail by way of examples.

EXAMPLE 1

Cloning of an Oxidoreductase from *Chloroflexus auratiacus* DSM 635

A) Cultivation of *Chloroflexus auratiacus* DSM 635

Cells of *Chloroflexus auratiacus* DSM 635 were cultivated in a bacterial incubator in the following medium (pH 8.2) at 48° C. under light: 0.1% yeast extract, 0.1% glycyl glycine, 0.01% $Na_2HPO_4 \times 2$ $H_2O$, 0.01% $MgSO_4 \times 7$ $H_2O$, 0.01% $KNO_3$, 0.05% $NaNO_3$, 0.01% NaCl, 0.005% $CaCl_2 \times 2H_2O$, 5 ml of a 0.01% Fe(III)citrate solution, 1 ml of trace element solution SL-6 [500 µl/l $H_2SO_4$, 2.28 g/l $MnSO_4 \times H_2O$, 500 mg/l $ZnSO_4 \times 7$ $H_2O$, 500 mg $H_3BO_3$, 25 mg/l $CuSO_4 \times 5$ $H_2O$, 25 mg/l $Na_2MoO_4 \times 2H_2O$, 45 mg/l $CoCl_2 \times 6 H_2O$]. On day 12 of the cultivation, cells were separated from the culture medium by centrifugation and stored at −80° C.

B) Amplification of the Gene Coding for Selective Oxidoreductase

Genomic DNA was extracted according to the method described in "Molecular Cloning" by Manniatis & Sambrook. The resulting nucleic acid served as a template for the polymerase chain reaction (PCR) involving specific primers which were derived from the gene sequence published under number 76258197 in the NCBI database. In doing so, the primers were provided in a 5'-terminal position with restriction sites for the endonucleases Nde I and Hind III or Sph I, respectively (SEQ ID NO:11, SEQ ID NO:12, SEQ ID NO:13), for subsequent cloning into an expression vector.

Amplification was carried out in a PCR buffer [10 mM Tris-HCl, (pH 8.0); 50 mM KCl; 10 mM $MgSO_4$; 1 mM dNTP Mix; in each case 20 pMol of primer and 2.5 U of Platinum Pfx DNA Polymerase (Invitrogen)] with 500 ng of genomic DNA and the following temperature cycles:

Cycle 1: 94° C., 2 min
Cycle 2×30:
   94° C., 30 sec
   56° C., 30 sec
   68° C., 60 sec
Cycle 3:
   68° C., 7 min
   4° C., ∞

The resulting PCR product with a size of about 750 bp was restricted after purification over a 1% agarose gel with the aid of the endonucleases Nde I and Hind III or endonucleases Sph I and Hind III, respectively, and was ligated into the backbone of the pET21a vector (Novagen) or of the pQE70 vector (Qiagen), respectively, which backbone had been treated with the same endonucleases. After transforming 2 µl of the ligation batch into E. coli Top 10 F' cells (Invitrogen), plasmid DNAs of ampicillin (or kanamycin)-resistant colonies were tested for the presence of an insert having a size of 750 bp by means of a restriction analysis with the endonucleases Nde I and Hind III or endonucleases Sph I and Hind III, respectively. Plasmid preparations from the clones which were positive for the fragment were subjected to a sequence analysis and subsequently transformed into Escherichia coli BL21 Star (Invitrogen) and E. coli RB791 (genetic stock, Yale), respectively.

EXAMPLE 2

Expression of Recombinant Chloroflexus Oxidoreductase in E. coli

The Escherichia coli strains BL21 Star (Invitrogen, Karlsruhe, Germany) and RB791 (E. coli genetic stock, Yale, USA), respectively, transformed with the expression construct were cultivated in 200 ml LB-medium (1% tryptone, 0.5% yeast extract, 1% NaCl) with ampicillin (50 µg/ml) or carbenicillin (50 µg/ml), respectively, until an optical density (OD) of 0.5, measured at 550 nm, was reached. The expression of recombinant protein was induced by adding isopropylthiogalactoside (IPTG) at a concentration of 0.1 mM. After 8 hours or 16 hours of induction at 25° C. and 220 rpm, the cells were harvested and frozen at −20° C. For the activity test, 10 mg of cells were mixed with 500 µl of 100 mM TEA buffer pH 7.0 and 500 µl of glass beads and digested for 10 min using a globe mill. The lysate obtained was then used in a diluted state for the respective measurements. The activity test was made up as follows: 870 µl of 100 mM TEA buffer pH 7.0, 160 µg NADH, 10 µl of diluted cell lysate. The reaction was started by adding 100 µl of a 100 mM substrate solution to the reaction mixture.

For enzyme recovery in large amounts, 30 g of cells were resuspended in 150 ml of triethanolamine buffer (100 mM, pH 7, 2 mM $MgCl_2$, 10% glycerol) and digested using a high-pressure homogenizer. Subsequently, the enzyme solution was mixed with 150 ml glycerol and stored at −20° C.

EXAMPLE 3

Cultivation of Organisms and Screening after a Reductive Conversion of Ethyl Secodione (Formula III)

For screening, the yeast strains Pichia farinosa DSM 70362, Candida gropengiesseri MUCL 29836, Candida vaccinii CBS 7318, Pichia farinosa DSM 3316, Saccharomyces cerevisiae CBS 1508 and Candida magnoliae CBS 6396 were cultivated in the following medium: yeast extract (5), peptone (5) and glucose (20) (the numbers in brackets are, in each case, g/l). The medium was sterilized at 121° C. and the yeasts were cultivated at 25° C. on a shaker at 140 revolutions per minute without further pH-adjustment.

The reductive conversion of ethyl secodione of formula III to the corresponding hydroxy secosteroid compound was tested in the following whole-cell biotransformation batches:

400 mg of freshly harvested cells were shaken in a batch with 50 mg glucose, 10 mg ethyl secodione of formula III and 900 µl of 100 mM trieethanolamine buffer (TEA) pH 7.0 at 28° C. and 1400 rpm for 24 hours. Subsequently, the batches were extracted with 1 ml of dichloromethane, centrifuged, dried with nitrogen and, after having been absorbed in acetonitrile, added to the HPLC analysis.

The screening results are summarized in Table 1.

TABLE 1

| Strain no. | Microorganism | Conversion of ethyl secodione after 24 hours with Wt strains Batch 24 h |
|---|---|---|
| DSM 70362 | Pichia farinosa | 0.7% |
| MUCL 29836 | Candida gropengiesseri | 0.2% |
| CBS 7318 | Candida vaccinii | 3.2% |
| DSM 3316 | Pichia farinosa | 15.8% |
| CBS 1508 | Saccharomyces cerevisiae | 0.7% |
| CBS 6396 | Candida magnoliae | 41% |

Strain CBS 6396 displayed the highest conversion of ethyl secodione and was thus chosen as the starting organism for the preparation of a cDNA library.

EXAMPLE 4

Preparation of a cDNA Library from Candida magnoliae CBS 6396 and Cloning of Oxidoreductase A) Isolation (Total and mRNA) as Well as Preparation of the cDNA Library 600 mg of fresh cells were resuspended in 2.5 ml of ice-cold LETS buffer. 5 ml (about 20 g) of glass beads washed in nitric acid and equilibrated with 3 ml phenol (pH 7.0) were added to said cell suspension. The entire batch was then alternately treated by 30 sec of vortexing and 30 sec of cooling on ice, in total for 10 minutes. Subsequently, 5 ml of ice-cold LETS buffer was added, and this was again vigorously vortexed. Said cell suspension was centrifuged at 4° C. with 11000 g for 5 minutes. The aqueous phase was recovered and extracted twice with an equal volume of phenol:chloroform:isoamyl alcohol (24:24:1). This was subsequently followed by the extraction with chloroform. After the final extraction, the total RNA was precipitated at −20° C. for 4 h by adding 1/10 vol. of 5 M $LiCl_2$.

1 mg of total RNA thus obtained was used via Oligo-dT cellulose (NEB Biolabs) for the enrichment of the mRNA molecules. After the subsequent precipitation, 5 µg mRNA was used for the cDNA synthesis (pBluescript IIXR cDNA Library Construction kit, Stratagene). The library constructed according to the manufacturer's instructions was transformed into XL-10 Gold E. coli and screened for the activity of an ADH. A clone (cM4) was identified and isolated based on the decrease in absorbance with NADPH or NADH, respectively, as the cofactor and ethyl secodione (Formula III) as the substrate. The sequencing of the plasmid isolated from the clone with primer T7 and primer T3 resulted in an ORF of 789 bp. Said fragment coded for a fusion protein having a size of 262 amino acids and consisted of the a-fragment of the B-galactosidase and the sequence of a putative short-chain alcohol dehydrogenase.

B) Synthesis of a Full-length Transcript Coding for a Short-chain ADH from *Candida magnoliae* CBS 6396 by PCR Specific primers were constructed for subsequent cloning of the full-length transcript into the appropriate expression systems. In doing so, a 5'-primer with a recognition sequence for Nde I and Sph I, respectively, and a 3'-primer with a recognition sequence for XhoI and SacI, respectively, were modified (SEQ ID NO:14, SEQ ID NO:15, SEQ ID NO:16, SEQ ID NO:17). Plasmid DNA isolated from the clone (cM4) of the expression library of *Candida magnoliae* served as a template for the polymerase chain reaction. Amplification was carried out in a PCR buffer [10 mM Tris-HCl (pH 8.0); 50 mM KCl; 10 mM $MgSO_4$; 1 mM dNTP Mix; in each case 20 pMol of primer and 2.5 U of Platinum Pfx DNA Polymerase (Invitrogen)] with 50 ng of template and the following temperature cycles:

Cycle 1: 94° C., 2 min
Cycle 2×30:
　94° C., 15 sec
　58° C., 30 sec
　68° C., 75 sec
Cycle 3:
　68° C., 7 min
　4° C., ∞

The resulting PCR product was restricted after purification over a 1% agarose gel with the aid of the endonucleases Nde I and Xho I or the endonucleases Sph I and Sac I, respectively, and was ligated into the backbone of the pET21 a vector (Novagen) or of the pQME70 vector, respectively, which backbone had been treated with the same endonucleases. After transforming 2 nl of the ligation batch into *E. coli* Top 10 F' cells (Invitrogen), plasmid DNAs of ampicillin (or kanamycin)-resistant colonies were tested for the presence of an insert having a size of 750 bp by means of a restriction analysis with the endonucleases Nde I and XhoI or the endonucleases Sph I and SacI, respectively. The expression constructs pET21-MgIV and pQME70-MgIV were sequenced. The gene from *Candida magnoliae* coding for a short-chain oxidoreductase had an open reading frame of a total of 729 bp (contained in SEQ ID NO:8), which corresponded to a protein of 243 amino acids (SEQ ID NO:3).

EXAMPLE 5

Expression of Recombinant Oxidoreductase in *E. coli* Cells

Competent *Escherichia coli* StarBL21(De3) cells (Invitrogen) and RB791 cells (*E. coli* genetic stock, Yale, USA), respectively, were transformed with the expression constructs pET21-MgIV and pQME70-MgIV, respectively, coding for the oxidoreductase. The *Escherichia coli* colonies transformed with the expression constructs were then cultivated in 200 ml of LB medium (1% tryptone, 0.5% yeast extract, 1% NaCl) with 50 µg/ml of ampicillin or 40 µg/ml of kanamycin, respectively, until an optical density of 0.5, measured at 550 nm, was reached. The expression of recombinant protein was induced by adding isopropylthiogalactoside (IPTG) at a concentration of 0.1 mM. After 16 hours of induction at 25° C. and 220 rpm, the cells were harvested and frozen at −20° C. For the activity test, 10 mg of cells were mixed with 500 µl of 100 mM TEA buffer pH 7.0, 1 mM $MgCl_2$ and 500 µl glass beads and digested for 10 min using a globe mill. The lysate obtained was then used in a diluted state for the respective measurements.

The activity test was made up as follows: 960 µl of 100 mM TEA buffer pH 7.0, 1 bmM $MgCl_2$, 160 µg NADPH, 10 µl of diluted cell lysate. The reaction was started by adding 10 µl of a 100 mM substrate solution in 70% methanol to the reaction mixture.

For enzyme recovery in large amounts, 30 g of cells were resuspended in 150 ml of triethanolamine buffer (100 mM, pH 7, 2 mM $MgCl_2$, 10% glycerol) and digested using a high-pressure homogenizer. Subsequently, the enzyme solution was mixed with 150 ml glycerol and stored at −20° C.

EXAMPLE 6

Reduction of Ethyl Secodione (Formula III) via Oxidoreductase SEQ ID NO:1

For the reduction of ethyl secodione (Formula III), a mixture of 800 µl buffer (100 mM potassium phosphate, pH=7, 2 mM $MgCl_2$), 1.2 ml 2-propanol, 0.08 mg NAD, 100 mg ethyl secodione (Formula III) and 1 ml of the enzyme suspension oxidoreductase SEQ ID NO:1 (see Example 3) was incubated in a reaction vessel at room temperature for 24 h under constant thorough mixing. After 96 h, >90% of the ethyl secodione (Formula III) used had been reduced.

Upon completion of the reaction, the reaction mixture was reprocessed by extraction with dichloromethane, the organic phase containing the product was separated and the 17-beta-hydroxy compound (ethyl secol) was obtained by evaporating/distilling off the solvent.

The conversion of the ethyl secodione into ethyl secol was followed via HPLC. For this purpose, a separating column EC125/4 Nucleodur 100-5 C18ec (Machery-Nagel, Düren, Germany) with acetonitrile and water as solvents was used. For analytics, a linear gradient of the acetonitrile portion in the solvent from 30% to 70% was applied. Identification of the reaction products was performed by comparison with reference substances.

EXAMPLE 7

Reduction of Ethyl Secodione (Formula III) via Oxidoreductase SEQ ID NO:2

For the reduction of ethyl secodione (Formula III), a mixture of 250 µl buffer (100 mM triethanolamine, pH=8, 2 mM $MgCl_2$), 250 µl 4-methyl-2-pentanol, 0.02 mg NAD, 25 mg ethyl secodione (Formula III) and 25 µl of the enzyme suspension oxidoreductase SEQ ID NO:2 (see Example 3) was incubated in a reaction vessel at room temperature for 96 h under constant thorough mixing. After 96 h, >30% of the ethyl secodione (Formula III) used had been reduced to the hydroxy compound.

Upon completion of the reaction, the reaction mixture was reprocessed by extraction with dichloromethane, the organic phase containing the product was separated and the 17-beta-hydroxy compound (ethyl secol) was obtained by evaporating/distilling off the solvent.

EXAMPLE 8

Reduction of Ethyl Secodione (Formula III) via Oxidoreductase SEQ ID NO:3

For the reduction of ethyl secodione (Formula III), a mixture of 100 µl buffer (100 mM triethanolamine, pH=7, 2 mM $MgCl_2$), 400 µl 4-methyl-2-pentanol, 0.02 mg NADP, 25 mg ethyl secodione (Formula III) and 100 µl of the enzyme suspension oxidoreductase SEQ ID NO:3 (see Example 3) was incubated in a reaction vessel at room temperature for 72 h under constant thorough mixing. After 72 h, >95% of the ethyl secodione (Formula III) used had been reduced to the hydroxy compound.

EXAMPLE 9

Reduction of Ethyl Secodione (Formula III) via Oxidoreductase SEQ ID NO:4

For the reduction of ethyl secodione (Formula III), a mixture of 200 µl buffer (100 mM triethanolamine, pH=9, 2 mM MgCl$_2$), 300 µl 2-heptanol, 0.025 mg NADP, 100 mg ethyl secodione (Formula III) and 50 µl of the enzyme suspension oxidoreductase SEQ ID NO:4 (see Example 3) was incubated in a reaction vessel at room temperature for 72 h under constant thorough mixing. After 72 h, >80% of the ethyl secodione (Formula III) used had been reduced to the hydroxy compound.

EXAMPLE 10

Reduction of Ethyl Secodione (Formula III) Via Oxidoreductase SEQ ID NO:5

For the reduction of ethyl secodione (Formula III), a mixture of 300 µl buffer (100 mM triethanolamine, pH=7, 2 mM MgCl$_2$), 1.2 ml 4-methyl-2-pentanol, 0.12 mg NADP, 150 mg ethyl secodione (Formula III) and 0.6 ml of the enzyme suspension oxidoreductase SEQ ID NO:5 (see Example 3) was incubated in a reaction vessel at room temperature for 72 h under constant thorough mixing. After 72 h, >90% of the ethyl secodione (Formula III) used had been reduced to the hydroxy compound.

---

The invention claimed is:

1. An isolated polypeptide having oxidoreductase activity, selected from the group consisting of:
   (a) a polypeptide having the amino acid sequence of SEQ ID NO: 3,
   (b) a polypeptide having an amino acid sequence encoded by the nucleic acid sequence of SEQ ID NO: 8, and
   (c) a polypeptide having an amino acid sequence encoded by a nucleic acid sequence that hybridizes to the nucleic acid sequence of SEQ ID NO: 8 under stringent conditions, wherein said stringent conditions comprise hybridization in a 0.7-1.0 M NaCl solution at 60° C.

2. An isolated polypeptide according to claim 1 obtained from *Candida magnoliae* CBS 6396.

3. A method for the reduction of secodione derivatives of formula I

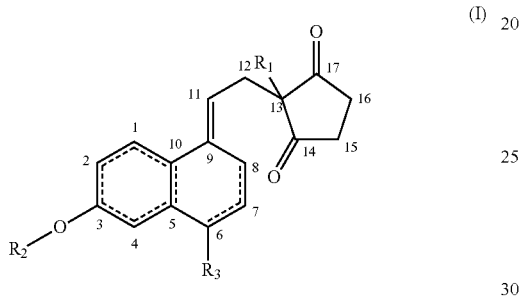

(I)

wherein,
   $R_1$ is hydrogen or a $C_1$-$C_4$ alkyl group,
   $R_2$ is hydrogen, a $C_1$-$C_8$ alkyl group or a protective group for OH,
   $R_3$ is hydrogen, a methyl group or a halide,
   the structural element

represents a benzene ring or a $C_6$ ring having 0, 1 or 2 C—C double bonds, wherein,
   a double bond is optionally included at positions 6/7 or 7/8, and
   the carbon at positions 1, 2, 4, 5, 6, 7, 8, 9, 11, 12 and 16 is independently substituted with hydrogen, a $C_1$-$C_4$ alkyl group, a halide or a phenyl group,
the method comprising:
   (a) exposing a secodione derivative of formula I to the polypeptide of claim 1; and
   (b) obtaining a reduced secodione derivative.

4. The method of claim 3, wherein the secodione derivative of formula I is reduced in the presence of NADH or NADPH as a cofactor.

5. The method of claim 4, wherein the secodione derivative of formula I is used in a reaction batch, wherein the the cofactor at a concentration of $\geq 10$ g/l.

6. The method of claim 4, wherein NADH or NADPH is oxidized to NAD or NADPH by the polypeptide and cofactor is regenerated continuously.

7. An isolated polypeptide having oxidoreductase activity, wherein the polypeptide
   a) comprises the amino acid sequence SEQ ID No:3 or
   b) is encoded by the nucleic acid sequence SEQ ID No:8, and wherein the polypeptide has the activity of reducing the secodione derivative of Formula I in the presence of a cofactor NADH or NADPH

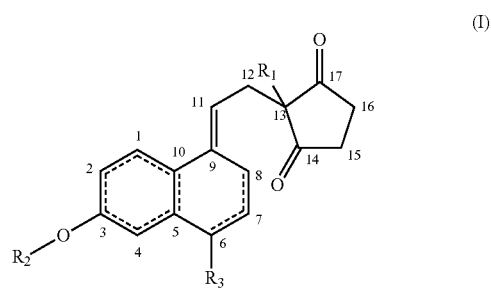

(I)

wherein,
   $R_1$ is hydrogen or a $C_1$-$C_4$ alkyl group,
   $R_2$ is hydrogen, a $C_1$-$C_8$ alkyl group or a protective group for OH,
   $R_3$ is hydrogen, a methyl group or halide,
   the structural element

represents a benzene ring or a $C_6$ ring having 0, 1 or 2 C—C double bonds, wherein,
   a double bond is optionally included at positions 6/7 or 7/8, and
   the carbon at positions 1, 2, 4, 5, 6, 7, 8, 9, 11, 12 and 16 is independently substituted with hydrogen, a $C_1$-$C_4$ alkyl group, a halide or a phenyl group.

8. The polypeptide according to claim 7, wherein $R_2$ is a protective group for OH and is an ester.

9. An isolated polypeptide according to claim 7, obtained from *Candida magnoliae*.

10. An isolated polypeptide having oxidoreductase activity, wherein the polypeptide is encoded by a nucleic acid sequence which hybridizes to SEQ ID No:8 under stringent conditions, wherein said stringent conditions comprise hybridization in a 0.7-1.0 M NaCl solution at 60° C., and wherein said polypeptide is capable of reducing the secodione derivative of Formula I in the presence of a cofactor NADH or NADPH

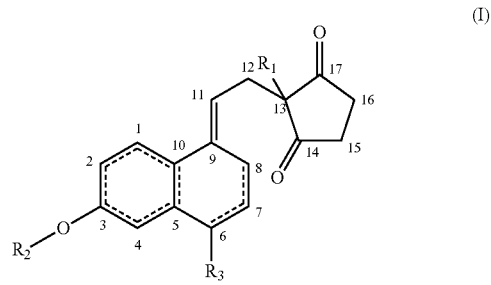

(I)

wherein,
R$_1$ is hydrogen or a C$_1$-C$_4$ alkyl group,
R$_2$ is hydrogen, a C$_1$-C$_8$ alkyl group or a protective group for OH,
R$_3$ is hydrogen, a methyl group or halide,
the structural element

represents a benzene ring or a C$_6$ ring having 0, 1 or 2 C—C double bonds, wherein,
a double bond is optionally included at positions 6/7 or 7/8, and
the carbon at positions 1, 2, 4, 5, 6, 7, 8, 9, 11, 12 and 16 is independently substituted with hydrogen, a C$_1$-C$_4$ alkyl group, a halide or a phenyl group.

11. The polypeptide according to claim 10, wherein R$_2$ is a protective group for OH and is an ester.

12. An isolated polypeptide according to claim 10, obtained from *Candida Magnoliae*.

* * * * *

UNITED STATES PATENT AND TRADEMARK OFFICE
CERTIFICATE OF CORRECTION

| | | |
|---|---|---|
| PATENT NO. | : 8,323,936 B2 | Page 1 of 1 |
| APPLICATION NO. | : 13/227390 | |
| DATED | : December 4, 2012 | |
| INVENTOR(S) | : Gupta et al. | |

It is certified that error appears in the above-identified patent and that said Letters Patent is hereby corrected as shown below:

<u>Title Page, Item (30) Left-hand Column</u>
In Prior Publication Data, add the Foreign Priority Information --A 2027/2006 AT Dec. 7, 2006--

<u>Column 37</u>
Line 58, change "the the" to --the--
Line 59, change "cofactor at" to --cofactor is at--

Signed and Sealed this
Twenty-fourth Day of September, 2013

Teresa Stanek Rea
*Deputy Director of the United States Patent and Trademark Office*